(12) United States Patent
Nakagawa et al.

(10) Patent No.: US 12,042,877 B2
(45) Date of Patent: Jul. 23, 2024

(54) WELDING MANAGEMENT SYSTEM

(71) Applicant: HITACHI, LTD., Tokyo (JP)

(72) Inventors: Ryoji Nakagawa, Tokyo (JP); Hisashi Endou, Tokyo (JP); Hiroshi Yoshikawa, Tokyo (JP); Toshihiro Yamada, Tokyo (JP); Nobuhiro Kakeno, Tokyo (JP); Hideya Isaka, Tokyo (JP)

(73) Assignee: HITACHI, LTD., Tokyo (JP)

( * ) Notice: Subject to any disclaimer, the term of this patent is extended or adjusted under 35 U.S.C. 154(b) by 1191 days.

(21) Appl. No.: 16/640,636

(22) PCT Filed: Mar. 30, 2018

(86) PCT No.: PCT/JP2018/013655
§ 371 (c)(1),
(2) Date: Feb. 20, 2020

(87) PCT Pub. No.: WO2019/064654
PCT Pub. Date: Apr. 4, 2019

(65) Prior Publication Data
US 2020/0361023 A1    Nov. 19, 2020

(30) Foreign Application Priority Data

Sep. 27, 2017    (JP) ................. 2017-186804

(51) Int. Cl.
*B23K 11/25*    (2006.01)
*B23K 11/16*    (2006.01)
(Continued)

(52) U.S. Cl.
CPC ............ *B23K 11/252* (2013.01); *B23K 11/16* (2013.01); *B23K 31/125* (2013.01); *G01N 27/82* (2013.01);
(Continued)

(58) Field of Classification Search
CPC ... G01D 5/145; G01D 2205/80; G01D 3/0365
See application file for complete search history.

(56) References Cited

U.S. PATENT DOCUMENTS 6,057,523 A    5/2000  Fujii et al.
2003/0020454 A1  1/2003  Hauer
(Continued)

FOREIGN PATENT DOCUMENTS

CN    1179372 A    4/1998
JP    S61-138480 U  8/1986
(Continued)

OTHER PUBLICATIONS

International Search Report and Written Opinion for related International Application No. PCT/JP2018/013655, mailed on Jun. 12, 2018; English translation of ISR provided (10 pages).
(Continued)

*Primary Examiner* — Jermele M Hollington
*Assistant Examiner* — Temilade S Rhodes-Vivour
(74) *Attorney, Agent, or Firm* — PROCOPIO, CORY, HARGREAVES & SAVITCH LLP

(57) ABSTRACT

Provided is a welding management system that appropriately manages welding. The welding management system (100) includes a plurality of local magnetic sensors (10a to 10f) provided around a target joining position (K) and a correction magnetic sensor (20) curved to surround the target joining position (K). A data processing unit (30) generates information of a joining state of the target joining position (K) based on a difference between a detection value of each of the plurality of local magnetic sensors (10a to 10f) and a detection value of the correction magnetic sensor (20).

8 Claims, 12 Drawing Sheets

(51) Int. Cl.
    *B23K 31/12*     (2006.01)
    *B23K 101/36*     (2006.01)
    *G01N 27/82*     (2006.01)
    *G01N 33/207*     (2019.01)

(52) U.S. Cl.
    CPC ........ *G01N 33/207* (2019.01); *B23K 2101/36* (2018.08)

(56) References Cited

U.S. PATENT DOCUMENTS

| | | | | |
|---|---|---|---|---|
| 2007/0247224 | A1* | 10/2007 | May | G01D 5/24476 330/63 |
| 2010/0141242 | A1* | 6/2010 | Abe | G01D 5/145 324/207.11 |
| 2011/0094474 | A1* | 4/2011 | Ikeda | G01D 11/245 264/277 |
| 2013/0057288 | A1 | 3/2013 | Ogata et al. | |
| 2016/0161286 | A1* | 6/2016 | Oeda | G01D 5/145 324/207.2 |
| 2016/0223358 | A1* | 8/2016 | Ausserlechner | G01D 5/145 |

FOREIGN PATENT DOCUMENTS

| | | |
|---|---|---|
| JP | 2003-344515 A | 12/2003 |
| JP | 2004-500689 A | 1/2004 |
| JP | 2008139233 A | 6/2008 |
| JP | 2013-54984 A | 3/2013 |
| WO | 2010/146939 A1 | 12/2010 |

OTHER PUBLICATIONS

The First Office Action for related Chinese Patent Application No. 201880051120.0, mailed on Mar. 3, 2021; English translation provided, (15 pages).

* cited by examiner

WELDING MANAGEMENT SYSTEM

CROSS-REFERENCE TO RELATED APPLICATIONS

This application is a U.S. National Stage entry of PCT Application No: PCT/JP2018/013655 filed Mar. 30, 2018, which claims priority to Japanese Patent Application No. 2017-186804, filed Sep. 27, 2017, the contents of which are incorporated herein by reference.

TECHNICAL FIELD

The present invention relates to a welding management system.

BACKGROUND ART

A technique disclosed in PTL 1 is known as an example of a technique of visualizing current distribution inside a lithium-ion battery. That is, PTL 1 discloses that "a difference between a magnetic field generated from the lithium-ion battery and a correction magnetic field recorded by a recording unit" is calculated and "electric current distribution in the lithium-ion battery" is calculated "based on the difference". The "correction magnetic field" is magnetism in the vicinity of the lithium-ion battery and is a value detected in advance by a magnetic sensor in a state in which no voltage or the like is applied to terminals of the lithium-ion battery.

CITATION LIST

Patent Literature

PTL 1: JP-A-2013-54984

SUMMARY OF INVENTION

Technical Problem

As described above, PTL 1 discloses a technique of visualizing the current distribution inside the lithium-ion battery. In a case of "welding" such as resistance welding, it is required to know current distribution inside a member to be welded. The resistance welding is a welding method in which members to be welded abut against each other (or are superimposed) and are energized in a pressurized state and a joining surface is fixed by Joule heat.

It is desirable that current distribution of the joining surface is uniform when the members to be welded are energized in the above-described resistance welding. However, the current distribution of the joining surface is non-uniform due to surface roughness or pressure distribution of the joining surface and an influence of impurities or the like that are adhered to the joining surface. As a result, welding quality is poor.

Here, with reference to the technique disclosed in PTL 1, it is considered to provide a plurality of magnetic sensors around the joining surface of the members to be welded and know the current distribution of the joining surface based on detection values.

However, a small variation width of a portion indicating defective welding in a waveform of a magnetic signal is very small in many cases. Provided that a detection range of the magnetic sensors matches a variation width of the entire waveform of the magnetic signal, a quantization width accompanying with an A/D conversion at the time of signal recording increases accordingly, resulting in low accuracy of detecting defective welding.

Although a cancel coil that cancels magnetic noise is also provided in PTL 1, there is room for improvement in such a configuration for the following reasons. For example, even when a magnetic signal in a normal state (that is, when welding is appropriately performed) is stored as the "magnetic noise" in advance and the "magnetic noise" is canceled by the cancel coil, it is not always possible to appropriately extract a waveform of the portion indicating defective welding.

This is because the magnetic signal accompanying with welding changes transiently, and the waveform of the magnetic signal is slightly different for members to be welded depending on deterioration of an electrode or a pressurizer used for welding and states of an end surface (a welding surface) of the members to be welded. It is desirable to appropriately manage welding and maintain and improve welding quality. However, as described above, PTL 1 does not disclose such a technique.

An object of the invention is to provide a welding management system that appropriately manages welding.

Solution to Problem

To solve the problems described above, the invention provides a welding management system. The welding management system includes a magnetic detection unit and a data processing unit. The magnetic detection unit includes a plurality of first magnetic detection units provided around a target joining position and a second magnetic detection unit curved to surround the target joining position. The data processing unit generates information of a joining state of the target joining position based on a difference between a detection value of each of the plurality of the first magnetic detection units and a detection value of the second magnetic detection unit.

Advantageous Effect of Invention

According to the invention, the welding management system that appropriately manages welding can be provided.

DESCRIPTION OF EMBODIMENTS

First Embodiment

Figure 1:
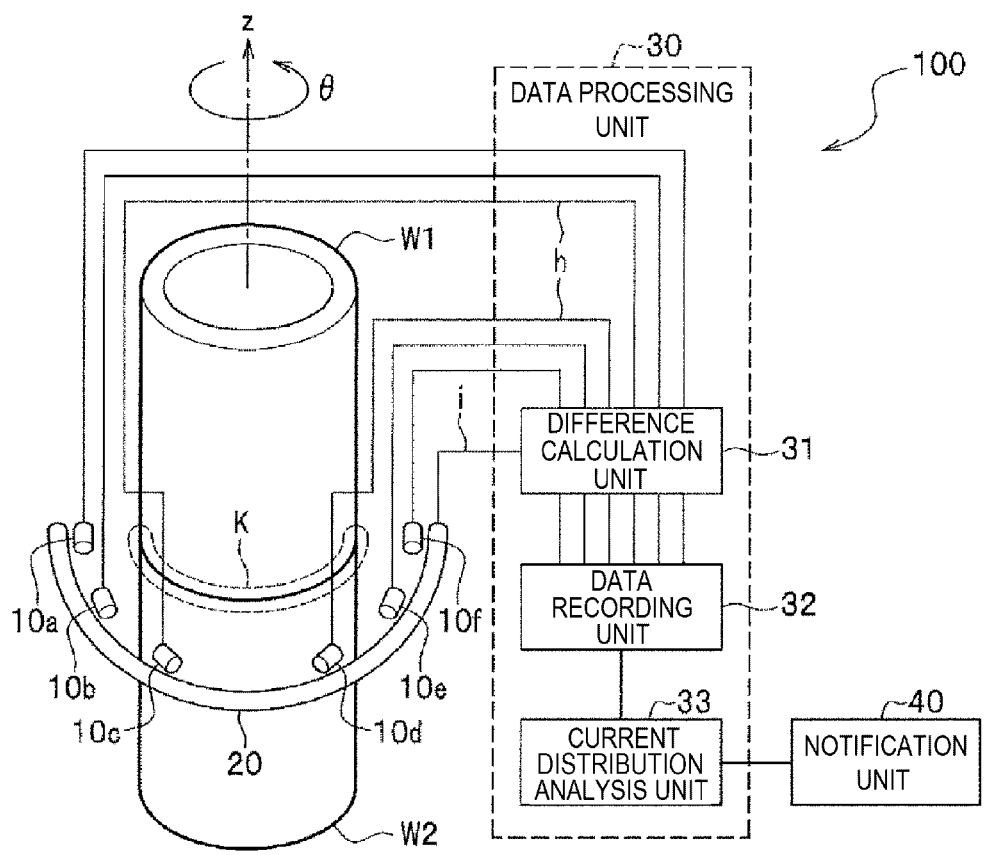
FIG. 1 is a view showing a welding management system according to a first embodiment of the invention.

FIG. 1 is a view showing a welding management system 100 according to the first embodiment of the invention.

As shown in FIG. 1, a central axis of cylindrical members to be welded W1 and W2 is a z axis. A moving radial direction with the z axis as a reference is a θ direction (also referred to as a "circumferential direction"). Hereinafter, an example in which resistance welding is performed in a state in which end surfaces of the members to be welded W1 and W2 abut against each other will be described.

The welding management system 100 manages welding of the members to be welded W1 and W2 and monitors whether defective welding occurs. As shown in FIG. 1, the welding management system 100 includes local magnetic sensors 10a to 10f (a first magnetic detection unit), a correction magnetic sensor 20 (a second magnetic detection unit), a data processing unit 30, and a notification unit 40.

The local magnetic sensors 10a to 10f locally detect magnetism around a target joining position K of the members to be welded W1 and W2. In FIG. 1, six local magnetic sensors 10a to 10f are provided around the target joining position K. The "target joining position K" is a position to be joined during welding. In FIG. 1, the "target joining position K" is in the vicinity of abutting surfaces of the members to be welded W1 and W2.

An example of the local magnetic sensors 10a to 10f may include a search coil. The search coil includes a coil wound in a solenoid shape and detects magnetism based on an induced voltage generated in the coil. In this manner, each of the local magnetic sensors 10a to 10f includes a "coil" used for magnetic detection. Accordingly, magnetism (or an induced voltage) around the target joining position K can be detected at low cost and with high accuracy.

When a current accompanying with energization of the members to be welded W1 and W2 flows in a z axial direction, a magnetic field is generated in the θ direction according to the Biot-Savart law. The local magnetic sensors 10a to 10f are provided such that a magnetic force line of the magnetic field passes through the coil (not shown). When there is a change in interlinkage magnetic fluxes of the local magnetic sensors 10a to 10f, induced voltages that are proportional to temporal differentiations of the interlinkage magnetic fluxes are generated in coils of the local magnetic sensors 10a to 10f so as to cancel the change. Local magnetism in the vicinity of the target joining position K is detected based on the induced voltages.

The correction magnetic sensor 20 shown in FIG. 1 detects global (uniform in the circumferential direction) magnetism in the vicinity of the target joining position K. An example of such a correction magnetic sensor 20 may include a Rogowski coil. The Rogowski coil has a configuration in which the entire coil has a solenoid shape and is curved in a circular arc shape. A detection principle of the Rogowski coil is the same as the search coil described above. In this manner, the correction magnetic sensor 20 also includes a "coil" used for magnetic detection.

As shown in FIG. 1, the correction magnetic sensor 20 is curved to surround the target joining position K. The expression "surround the target joining position K" not only includes a case in which the target joining position K is substantially completely surrounded (that is, in a range of θ=0° to 360°), but also includes a case in which the target joining position K is partially surrounded (for example, in a range of θ=0° to 180°).

The expression of the correction magnetic sensor 20 being "curved" not only includes a case in which the correction magnetic sensor 20 is curved into a circular arc shape, but also includes a case in which the correction magnetic sensor 20 is curved into a quadrangular frame shape.

Figure 2:
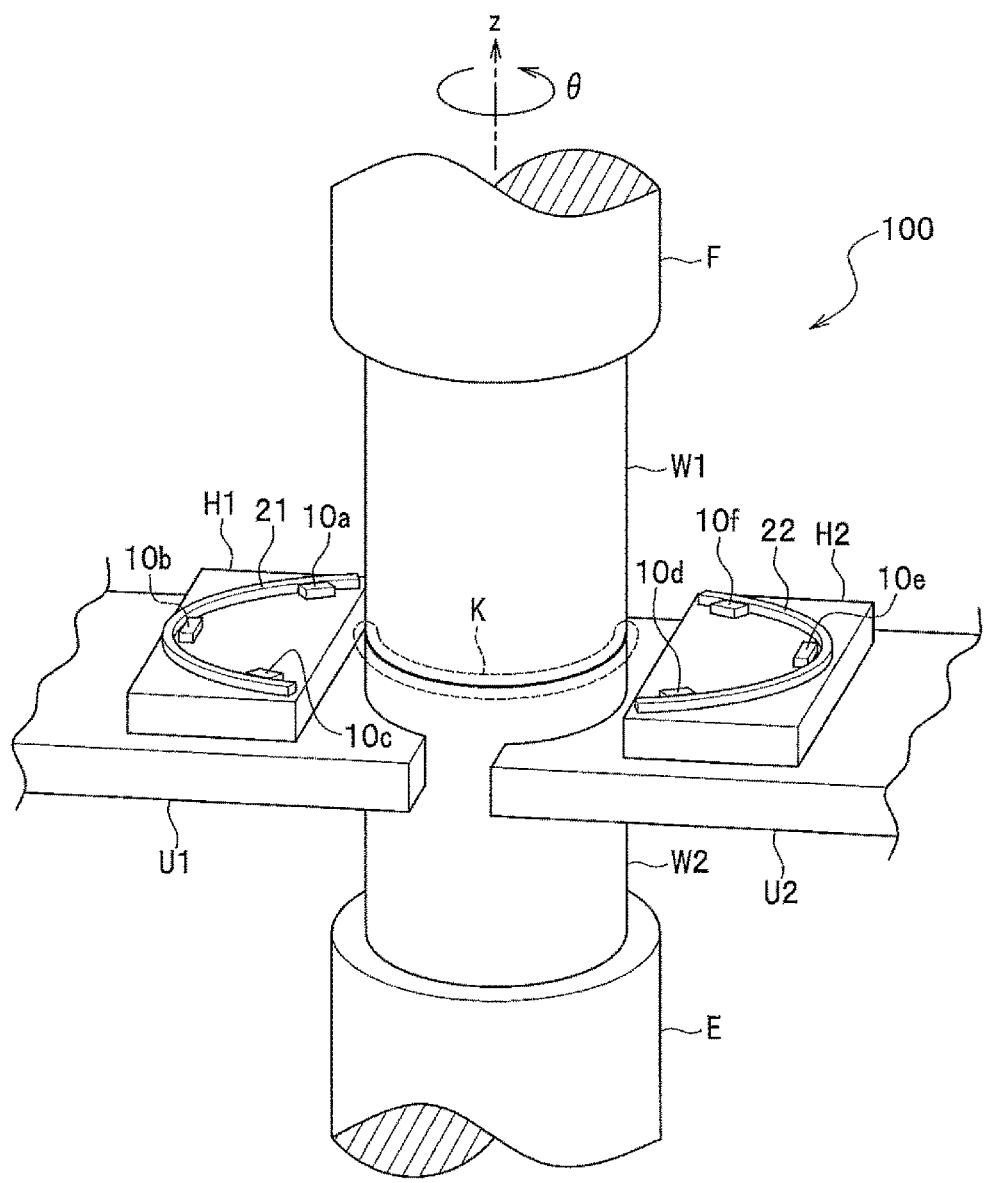
FIG. 2 is a perspective view showing an arrangement of local magnetic sensors, correction magnetic sensors, and the like that are provided in the welding management system according to the first embodiment of the invention.

The correction magnetic sensor 20 is shown in a simplified manner in FIG. 1. In practice, two correction magnetic sensors 21 and 22 that form the correction magnetic sensor 20 (see FIG. 1) are provided as shown in FIG. 2. More specifically, the correction magnetic sensors 21 and 22 having a semicircular shape in a plan view are provided in the vicinity of the target joining position Kin the z axial direction and are provided in the θ direction (that is, in a manner of surrounding the target joining position K).

When the members to be welded W1 and W2 are welded by heat accompanying with energization of the members to be welded W1 and W2, a "magnetic detection unit" that detects magnetism generated around the target joining position K accompanying with the energization includes the local magnetic sensors 10a to 10f and the correction magnetic sensors 21 and 22.

The data processing unit 30 shown in FIG. 1 has a function of processing (processing, recording, and analyzing) the detection value of the above-described "magnetic detection unit". The data processing unit 30 includes a difference calculation unit 31, a data recording unit 32, and a current distribution analysis unit 33.

The difference calculation unit 31 has a function of detecting a difference at every time point between a detection value of the local magnetic sensor 10a and a detection value of the correction magnetic sensor 20. Similarly, the difference calculation unit 31 has a function of detecting a difference at every time point between a detection value of each of the local magnetic sensors 10b to 10f and the detection value of the correction magnetic sensor 20.

As shown in FIG. 1, the difference calculation unit 31 is connected to the local magnetic sensors 10a to 10f via wires h and is also connected to the correction magnetic sensor 20 via another wire i.

The data recording unit 32 has a function of recording (storing) a calculation result of the difference calculation unit 31.

The current distribution analysis unit 33 performs a predetermined analysis on current distribution of the target joining position K using data recorded in the data recording unit 32. Processing of the difference calculation unit 31, the data recording unit 32, and the current distribution analysis unit 33 will be described below in detail.

The notification unit 40 notifies an administrator or the like of information generated by the data processing unit 30. Processing of the notification unit 40 will also be described below in detail.

FIG. 2 is a perspective view showing an arrangement of the local magnetic sensors 10a to 10f, the correction magnetic sensors 21 and 22, and the like. The wires h and the wire i (see FIG. 1) are omitted in FIG. 2.

In FIG. 2, the member to be welded W2 is supported by a pedestal E in a state in which the cylindrical members to be welded W1 and W2 abut against each other. A first electrode F is provided on an upper end surface of the member to be welded W1. A pair of second electrodes U1 and U2 are provided at predetermined positions facing each other on an outer circumferential surface of the members to be welded W1 and W2.

Amounting member H1 is fixed to the second electrode U1. The local magnetic sensors 10a to 10c and the correction magnetic sensor 21 are mounted on the mounting member H1. Similarly, a mounting member H2 is fixed to the second electrode U2. The local magnetic sensors 10d to 10f and the correction magnetic sensor 22 are mounted on the mounting member H2.

When a predetermined voltage is applied between the first electrode F and the second electrodes U1 and U2, a current flows in the z axial direction and heat is generated in the target joining position K to weld the members to be welded W1 and W2.

Figure 3:
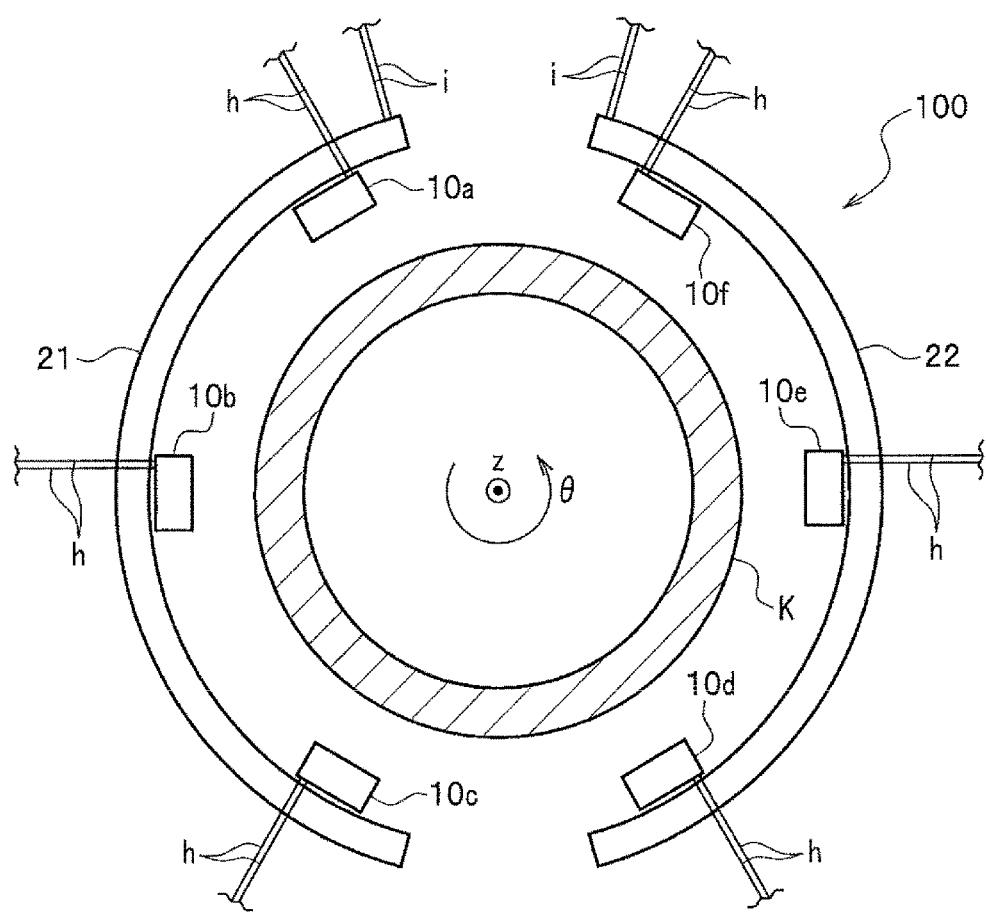
FIG. 3 is a cross-sectional view of the vicinity of a target joining position in the welding management system according to the first embodiment of the invention.

FIG. 3 is a cross-sectional view of a vicinity of the target joining position K.

The pedestal E (see FIG. 2), the first electrode F, the second electrodes U1 and U2, and the mounting members H1 and H2 are omitted in FIG. 3.

As shown in FIG. 3, the local magnetic sensors 10a to 10c and the correction magnetic sensor 21 are close to each other in the radial direction, and the local magnetic sensors 10d to 10f and the correction magnetic sensor 22 are close to each other in the radial direction.

The correction magnetic sensor 21 is provided to cover positions of the local magnetic sensors 10a to 10c in the circumferential direction (the θ direction). Similarly, the correction magnetic sensor 22 is provided to cover positions of the local magnetic sensors 10d to 10f in the circumferential direction.

That is, ranges in the circumferential direction of the correction magnetic sensors 21 and 22 that are curved to surround the target joining position K cover the positions of the plurality of local magnetic sensors 10a to 10f in the circumferential direction. According to such a configuration, the local magnetic sensors 10a to 10f can detect local magnetism in the circumferential direction and the correction magnetic sensors 21 and 22 can detect global magnetism in the circumferential direction.

Information of a joining state of the target joining position K is generated based on a difference between a detection value of each of the local magnetic sensors 10a to 10f and a detection value of the correction magnetic sensor 20 (the correction magnetic sensor 21 or the correction magnetic sensor 22). Hereinafter, processing of generating such information based on detection values (for example, induced voltages) of the local magnetic sensors 10a to 10f and the correction magnetic sensors 21 and 22 will be described. Magnetic flux density based on time integration of the induced voltages may be used as the detection values.

For example, a deviation of the current distribution of the target joining position K during energization may be generated due to surface roughness of the target joining position K (the joining surface) and impurities adhering to the target joining position K. This is because, in the target joining position K, a current flows concentratedly through a portion having a small electric resistance but hardly flows through a portion having a large electric resistance. In such a case, welding quality may be deteriorated in the portion having a large electric resistance since it is difficult to proceed fusion (or diffusion bonding).

When a deviation of the current distribution of the target joining position K is generated, the detection values of the local magnetic sensors 10a to 10f provided around the target joining position K vary or the manner of change of the detection values is abnormal in many cases. That is, the deviation of the current distribution of the target joining position K is reflected on the detection values of the local magnetic sensors 10a to 10f provided around the target joining position K.

Figure 4A:
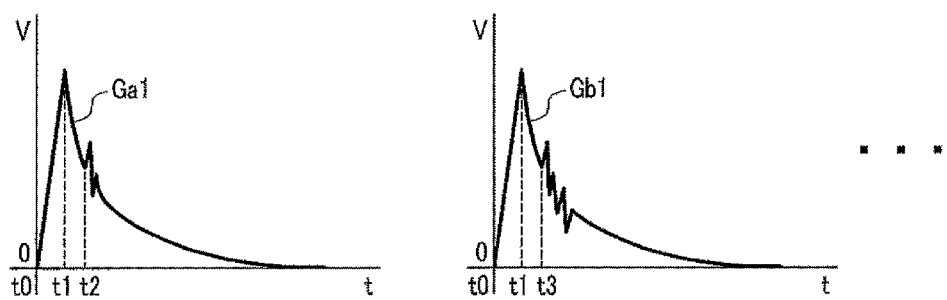
FIG. 4A shows an example of waveform diagrams of detection values of the local magnetic sensors provided in the welding management system according to the first embodiment of the invention.

FIG. 4A shows an example of waveform diagrams of the detection values of the local magnetic sensors 10a, 10b, . . . (see FIGS. 1 and 3 as appropriate).

In FIG. 4A, a vertical axis of a waveform diagram at the left side of a paper represents an induced voltage V detected by the local magnetic sensor 10a and a horizontal axis represents time t. A vertical axis of a second waveform diagram from the left of the paper represents an induced voltage V detected by the local magnetic sensor 10b and a horizontal axis represents time t.

FIG. 4A shows a waveform Ga1 of a detection value of the local magnetic sensor 10a and a waveform Gb1 of a detection value of the local magnetic sensor 10b. The remaining local magnetic sensors 10c to 10f are omitted.

When a predetermined voltage is applied between the first electrode F (see FIG. 2) and the second electrodes U1 and U2 (see FIG. 2) immediately after a time point t0, the magnetic field (magnetism) around the members to be welded W1 and W2 changes accompanying with a change in a current flowing through the members to be welded W1 and W2 (see FIG. 2). The detection values of the local magnetic sensors 10a to 10f also change so as to cancel the change of the magnetic field. In the example shown in FIG. 4A, the detection values of the local magnetic sensors 10a and 10b increase rapidly at time points from t0 to t1, and then decrease relatively slowly.

For example, when the current distribution of the target joining position K is deviated in the circumferential direction, the detection values of the local magnetic sensors 10a, 10b and the like change slightly in many cases. In the example shown in FIG. 4A, a small variation in the induced voltage V occurs immediately after a time point t2 in the waveform Ga1 or immediately after a time point t3 in the waveform Gb1. When such a variation is significant, defective welding may occur.

Figure 4B:
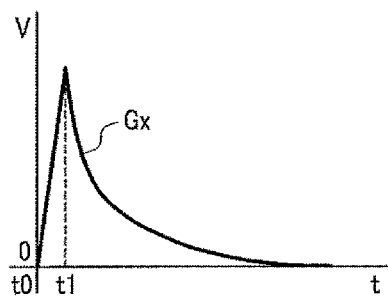
FIG. 4B shows an example of a waveform diagram of a detection value of a correction magnetic sensor provided in the welding management system according to the first embodiment of the invention.

FIG. 4B shows an example of a waveform diagram of the detection value of the correction magnetic sensor 21.

In FIG. 4B, a vertical axis represents an induced voltage V detected by the correction magnetic sensor 21 and a horizontal axis represents time t. Although the correction magnetic sensor 22 is omitted, a waveform of the detection value of the correction magnetic sensor 22 is the same as a waveform Gx of the detection value of the correction magnetic sensor 21.

The waveform Gx shown in FIG. 4B is similar to the waveforms Ga1, Gb1, . . . (see FIG. 4A) of the detection values of the local magnetic sensors 10a, 10b, . . . except that no small variation is present.

Even when the current distribution of the target joining position K is deviated, the deviation itself is rarely reflected on a global current in the target joining position K. This is because, for example, when a current hardly flows through a portion in the vicinity of the local magnetic sensors 10a and 10b due to an influence of surface roughness of the target joining position K (the joining surface) or the like, the current flows through other portions in the circumferential direction while avoiding the portion.

That is, even in a case where a position where a current is locally large and a position where a current is locally small are mixed in the target joining position K, a change of the global current is rarely influenced. Therefore, in the present embodiment, portions (nonuniform magnetic components in the circumferential direction: see FIG. 4C) where the waveforms Ga1, Gb1, . . . in FIG. 4A vary slightly are extracted based on the detection values (uniform magnetic components in the circumferential direction) detected by the correction magnetic sensor 21 at every time point.

That is, the data processing unit 30 shown in FIG. 1 generates the information of a joining state of the target joining position K based on a difference between the detection value of each of the local magnetic sensors 10a to 10c (see FIG. 3) and the detection value of the correction magnetic sensor 21 (see FIG. 3).

Similarly, the data processing unit 30 generates the information of a joining state of the target joining position K based on a difference between the detection value of each of the local magnetic sensors 10d to 10f (see FIG. 3) and the detection value of the correction magnetic sensor 22 (see FIG. 3).

When the current distribution in the target joining position K is uniform (that is, when the magnetic field of the target joining position K is uniform at every time point in the circumferential direction), the configuration may be as follows since the above-described difference is substantially zero. That is, the number of turns of the coils of the local magnetic sensors 10a to 10f may be equal to the number of turns of the coils of the correction magnetic sensors 21 and 22. A voltage dividing circuit (not shown) based on a predetermined turn ratio may be provided at a fore-stage of the difference calculation unit 31 (see FIG. 1).

Figure 4C:
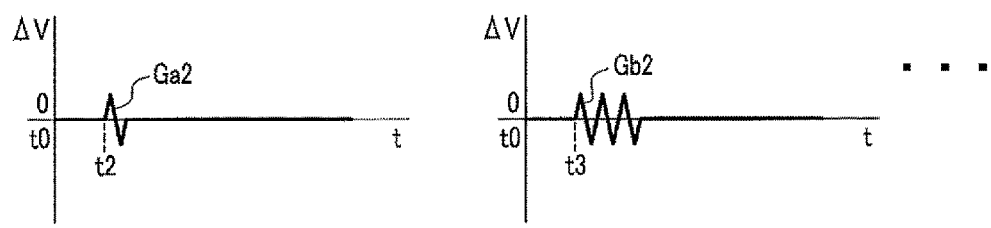
FIG. 4C shows waveforms obtained by calculating differences between the detection values of the local magnetic sensors and the detection value of the correction magnetic sensor in the welding management system according to the first embodiment of the invention.

FIG. 4C shows waveforms obtained by calculating a difference between the detection value of each of the local magnetic sensors 10a, 10b, . . . and the detection value of the correction magnetic sensor 21.

A waveform Ga2 shown in FIG. 4C is obtained by subtracting the detection value of the correction magnetic sensor 21 at every time point from the detection value of the local magnetic sensor 10a at every time point (for example, every 1 msec or every 1 usec). That is, the waveform Ga2 is obtained by extracting small variations in the waveform Ga1 shown in FIG. 4A.

A waveform Gb2 shown in FIG. 4C is obtained by subtracting the detection value of the correction magnetic sensor 21 at every time point from the detection value of the local magnetic sensor 10b at every time point. That is, the waveform Gb2 is obtained by extracting small variations in the waveform Gb1 shown in FIG. 4A.

Processing of calculating such a difference ΔV is performed by the difference calculation unit 31 shown in FIG. 1. The difference ΔV at every time point calculated by the difference calculation unit 31 is associated with identification information of the local magnetic sensors (for example, the local magnetic sensor 10a) and identification information of the members to be welded W1 and W2, and is recorded in the data recording unit 32 shown in FIG. 1.

Figure 4D:
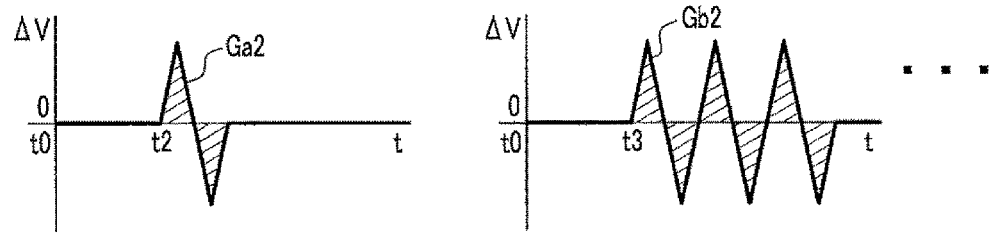
FIG. 4D is an enlarged view of apart of the waveforms shown in FIG. 4C.

FIG. 4D is an enlarged view of a part of the waveforms shown in FIG. 4C.

The current distribution analysis unit 33 shown in FIG. 1 calculates, for example, a time integration value (areas of shaded portions of the waveform Ga2) of an absolute value of the difference ΔV at every time point between the detection value of the local magnetic sensor 10a and the detection value of the correction magnetic sensor 21. The larger a degree of a deviation of the current distribution in the target joining position K, the larger the time integration value may be.

Similarly, the current distribution analysis unit 33 calculates time integration values of absolute values of differences ΔV for the detection values of the local magnetic sensors 10b to 10f. When one of the time integration values of the local magnetic sensors 10a to 10f is equal to or larger than a predetermined threshold, the current distribution analysis unit 33 determines that defective welding occurs. The "predetermined threshold" is a threshold used as a reference to determine whether defective welding occurs and is set in advance.

On the other hand, when none of the time integration values of the local magnetic sensors 10a to 10f is equal to or larger than a predetermined threshold, the current distribution analysis unit 33 determines that no defective welding occurs.

The current distribution analysis unit 33 stores information such as the time integration values of the absolute values of the differences ΔV between the detection values of the local magnetic sensors 10a to 10f and the correction magnetic sensors 21 and 22 and results of comparing the time integration values with the predetermined threshold as "information of a joining state".

Figure 5A:
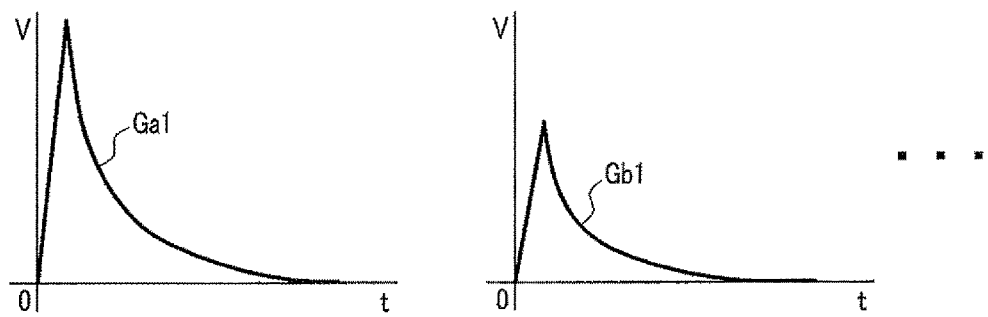
FIG. 5A shows another example of waveform diagrams of the detection values of the local magnetic sensors provided in the welding management system according to the first embodiment of the invention.

FIG. 5A shows another example of waveform diagrams of the detection values of the local magnetic sensors 10a, 10b, . . . (see FIGS. 1 and 3 as appropriate).

In the example shown in FIG. 5A, a maximum value of the detection value (the waveform Ga1) of the local magnetic sensor 10a is relatively large and a maximum value of the detection value (the waveform. Gb1) of the local magnetic sensor 10b is relatively small. Accordingly, defective welding caused by a deviation of current distribution may also occur when a variation of the detection values of the local magnetic sensors 10a, 10b, . . . is large.

Figure 5B:
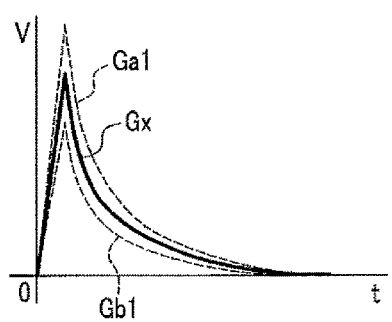
FIG. 5B shows a waveform diagram of the detection value of the correction magnetic sensor provided in the welding management system according to the first embodiment of the invention.

FIG. 5B shows a waveform diagram of the detection value of the correction magnetic sensor 21.

In FIG. 5B, a maximum value of the detection value (the waveform Gx) of the correction magnetic sensor 21 is smaller than the maximum value of the detection value (the waveform Ga1 represented by a broken line) of the local magnetic sensor 10a and is larger than the maximum value of the detection value of the local magnetic sensor 10b (the waveform Gb1 represented by a broken line).

Figure 5C:
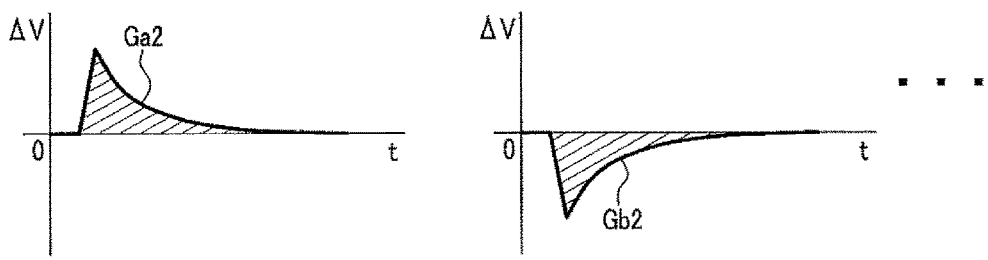
FIG. 5C shows waveforms obtained by calculating differences between the detection values of the local magnetic sensors and the detection value of the correction magnetic sensor in the welding management system according to the first embodiment of the invention.

FIG. 5C shows waveform diagrams obtained by calculating a difference between the detection value of each of the local magnetic sensors 10a, 10b, . . . and the detection value of the correction magnetic sensor 21.

The data processing unit 30 (see FIG. 1) generates information of a joining state of the target joining position K based on the difference $\Delta V$ at every time point between the detection value of the local magnetic sensor 10a and the detection value of the correction magnetic sensor 21. For example, the data processing unit 30 calculates time integration values (areas of shaded portions in FIG. 5C) of an absolute value of the difference $\Delta V$.

Figure 6:
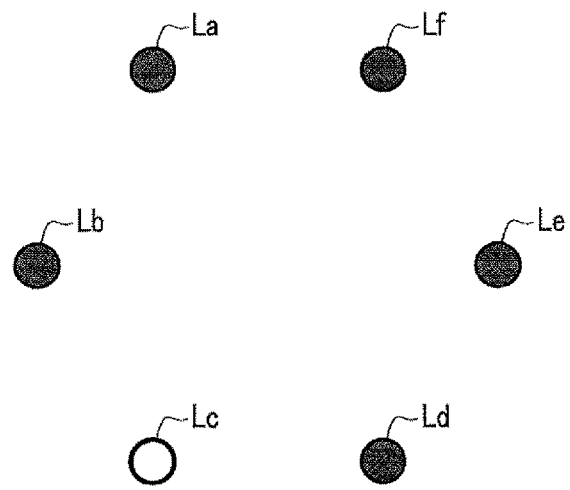
FIG. 6 is a view showing an analysis result of a current distribution analysis unit provided in the welding management system according to the first embodiment of the invention.

FIG. 6 is a view showing an analysis result of the current distribution analysis unit 33.

The welding management system 100 (see FIG. 1) includes light sources La to Lf shown in FIG. 6 as the notification unit 40 that notifies of information generated by the data processing unit 30.

The light source La is turned on when defective welding may occur in the vicinity of the local magnetic sensor 10a in the circumferential direction of the target joining position K, otherwise the light source La is turned off. Similarly, the light sources Lb to Lf are provided corresponding to the local magnetic sensors 10b to 10f.

In FIG. 6, six light sources La to Lf are provided (or displayed) corresponding to an arrangement of six local magnetic sensors 10a to 10f in a plan view (see FIG. 3). The light source La may be provided in the vicinity of the local magnetic sensor 10a or may be a predetermined pixel in a liquid crystal display (not shown). The same applies to the other light sources Lb to Lf.

In FIG. 6, the light source Lc is turned on and the light sources La, Lb, Ld to Lf are turned off. In this manner, when defective welding occurs in the target joining position K, the notification unit 40 displays the local magnetic sensor 10c corresponding to a position of the defective welding and the remaining local magnetic sensors 10a, 10b, 10d to 10f in a differentiated manner.

Accordingly, an administrator can take a measure immediately when defective welding occurs. For example, the administrator temporarily stops a machine such as a welding machine (not shown) or a conveying device (not shown), and specifies a reason for the defective welding (for example, deterioration of the first electrode F or the second electrodes U1 and U2: see FIG. 2) based on an analysis result of the current distribution analysis unit 33 or various examinations. Then, the administrator restarts each device after the reason for the defective welding is found out. Accordingly, poorly welded products can be prevented from being continuously produced.

Figure 7:
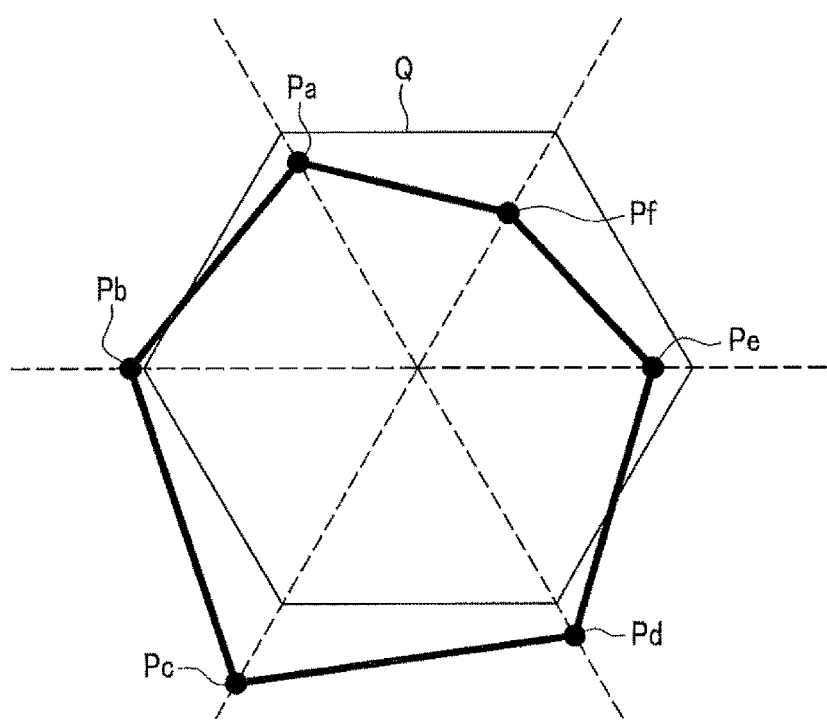
FIG. 7 is another view showing an analysis result of the current distribution analysis unit provided in the welding management system according to the first embodiment of the invention.

FIG. 7 is another view showing an analysis result of the current distribution analysis unit 33.

For example, the notification unit 40 (see FIG. 1) may display, as a radar chart as shown in FIG. 7, the detection values of the local magnetic sensors 10a to 10f at a time point (such as a peak time point of a welding current) when a predetermined time is elapsed after energization is started.

A point Pa shown in FIG. 7 represents the detection value of the local magnetic sensor 10a. Similarly, points Pb to Pf shown in FIG. 7 represent detection values of the local magnetic sensors 10b to 10f. A hexagonal reference line Q shown in FIG. 7 represents a reference value used for determining whether the detection values of the local magnetic sensors 10b to 10f are too large or too small. For example, the detection value of the correction magnetic sensor 21 may be used as the reference value.

In this manner, the notification unit 40 displays the detection values of the local magnetic sensors 10a to 10f as a radar chart by using the detection value of the correction magnetic sensor 21 as a reference.

For example, when the detection value of the local magnetic sensor 10a is smaller than the detection value of the correction magnetic sensor 21 (when the difference $\Delta V$ is a negative value), the detection value of the local magnetic sensor 10a is plotted inward of the reference line Q.

On the other hand, when the detection value of the local magnetic sensor 10c is larger than the detection value of the correction magnetic sensor 21 (when the difference $\Delta V$ is a positive value), the detection value of the local magnetic sensor 10c is plotted outward of the reference line Q. It should be noted that processing of determining whether defective welding occurs is not necessary. For example, only the radar chart shown in FIG. 7 may be displayed.

In this manner, data relating to the current distribution of the target joining position K is visualized as the radar chart, so that the administrator can know a position where defective welding is likely to occur and can use the position where defective welding is likely to occur as a determination material at the time of specifying a reason for defective welding.

A plurality of radar charts as shown in FIG. 7 may be created based on detection values detected for every predetermined time during energization. Accordingly, the administrator can know how distribution of the detection values of the local magnetic sensors 10a to 10f in the radar chart changes with time.

<Effect>

According to the first embodiment, the information of the current distribution of the members to be welded W1 and W2 is generated based on the difference $\Delta V$ at every time point between the detection values of the local magnetic sensors 10a to 10f and the detection value (the uniform magnetic components in the circumferential direction) of the correction magnetic sensor 21 and the like. Accordingly, a detection range at the time of quantization can be set in advance in accordance with a change width of the difference $\Delta V$ (the nonuniform magnetic components in the circumferential direction). Therefore, even when the change width of the difference $\Delta V$ is very small, the difference $\Delta V$ can be detected with high accuracy.

Even when no defective welding occurs, the waveforms of the detection values of the local magnetic sensors 10a to 10f are slightly different in many cases for each of the members to be welded W1 and W2 that is sequentially conveyed. This is because microscopic states of welding surfaces are different for each of the members to be welded W1 and W2, and that devices such as the first electrode F, the second electrodes U1 and U2, and the pressurizer (not shown) gradually deteriorate.

Therefore, in the present embodiment, the uniform magnetic components (the induced voltages or the like) in the circumferential direction are detected for each of the members to be welded W1 and W2 by the correction magnetic sensors 21 and 22. Accordingly, a deviation from the uniform magnetic components (the nonuniform magnetic components in the circumferential direction) can be detected with high accuracy without being influenced by variations of the uniform magnetic components that are different for each of the members to be welded W1 and W2.

Provided that the correction magnetic sensors 21 and 22 are omitted, the detection value of the local magnetic sensor 10a is used as a reference, and a difference $\Delta V_A$ between the detection value of the local magnetic sensor 10a and each of the detection values of the local magnetic sensors 10b to 10f is calculated, it is less likely to detect defective welding. This is because a detection value of a counterpart local magnetic sensor (for example, the local magnetic sensor 10c) having the difference $\Delta V_A$ may be erroneously determined to be abnormal when the detection value of the local magnetic sensor 10a that is set as a reference is abnormal.

In contrast, in the present embodiment, the correction magnetic sensors 21 and 22 detect the uniform magnetic components in the circumferential direction each time welding is performed. Since the difference $\Delta V$ is calculated with the detection values of the correction magnetic sensors 21 and 22 as a reference, the erroneous determination described above can be prevented and welding can be appropriately managed.

<<Modification of the First Embodiment>>

Figure 8:
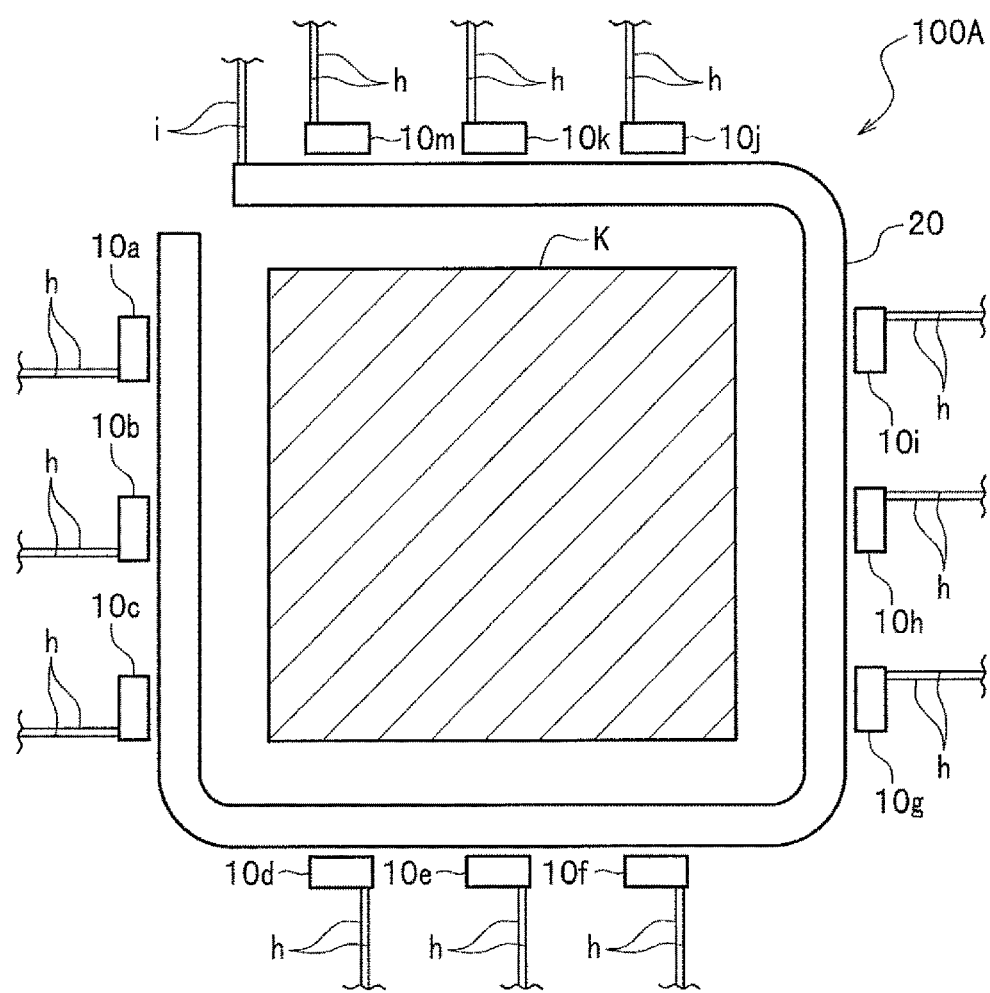
FIG. 8 is a cross-sectional view of the vicinity of a target joining position in a welding management system according to a modification of the first embodiment of the invention.

FIG. 8 is a cross-sectional view of the vicinity of the target joining position K in a welding management system 100A according to the modification of the first embodiment.

As shown in FIG. 8, for example, a cross-sectional shape of a member to be welded may be rectangular. If operation of a welding machine (not shown) is not interfered, as shown in FIG. 8, one correction magnetic sensor 20 that is curved into a quadrangular frame shape may be provided to surround the target joining position K and a plurality of local magnetic sensors 10a to 10m may be provided in the vicinity of the correction magnetic sensor 20. Since processing performed by the data processing unit 30 (see FIG. 1) is the same as the processing in the first embodiment, a description thereof will be omitted.

Second Embodiment

The second embodiment is different from the first embodiment in that coils of the local magnetic sensors 10a to 10c (see FIG. 9) are wound on the correction magnetic sensor 21 and coils of the local magnetic sensors 10d to 10f are wound on the correction magnetic sensor 22. The other parts (a configuration of or processing performed by the data processing unit 30) are the same as those in the first embodiment. Therefore, a difference from the first embodiment will be described and a description of repeated parts will be omitted.

Figure 9:
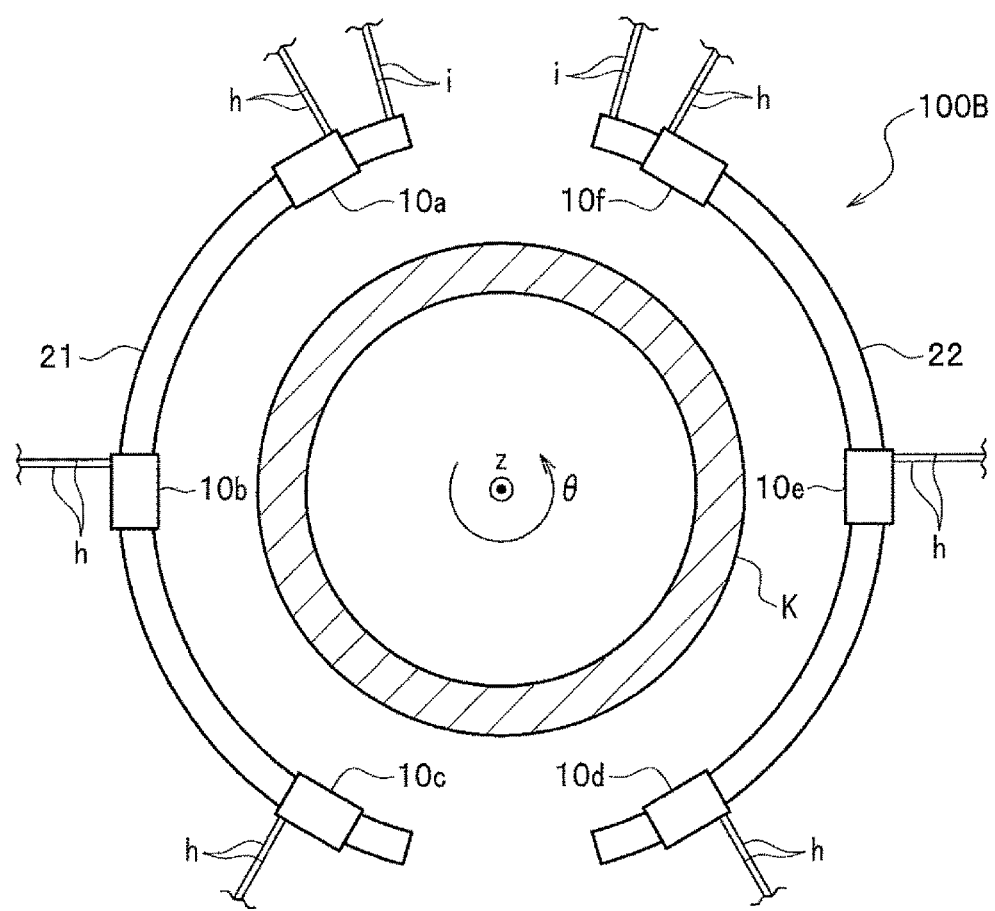
FIG. 9 is a cross-sectional view of the vicinity of a target joining position in a welding management system according to a second embodiment of the invention.

FIG. 9 is a cross-sectional view of the vicinity of the target joining position K.

As shown in FIG. 9, a welding management system 100B includes the local magnetic sensors 10a to 10f provided around the target joining position K and the correction magnetic sensors 21 and 22 curved to surround the target joining position K.

Three local magnetic sensors 10a to 10c are wound on the correction magnetic sensor 21. Three local magnetic sensors 10d to 10f are wound on the correction magnetic sensor 22. Then, information of a joining state in the target joining position K is generated based on a difference at every time point between a detection value of each of the local magnetic sensors 10a to 10f and a detection value of the correction magnetic sensors 21 and 22.

<Effect>

According to the second embodiment, the correction magnetic sensor 21 also serves as a space used for providing the local magnetic sensors 10a to 10c and the correction magnetic sensor 22 also serves as a space used for providing the local magnetic sensors 10d to 10f. Therefore, a space used for providing a "magnetic detection unit" (the local magnetic sensors 10a to 10f and the correction magnetic sensors 21 and 22) can be reduced compared to the first embodiment.

Third Embodiment

The third embodiment is different from the first embodiment in that parts of the correction magnetic sensors 21 and 22 (see FIG. 10) also function as the local magnetic sensors 10a to 10f. The other parts (a configuration of or processing performed by the data processing unit 30) are the same as those in the first embodiment. Therefore, a difference from the first embodiment will be described and a description of repeated parts will be omitted.

Figure 10:
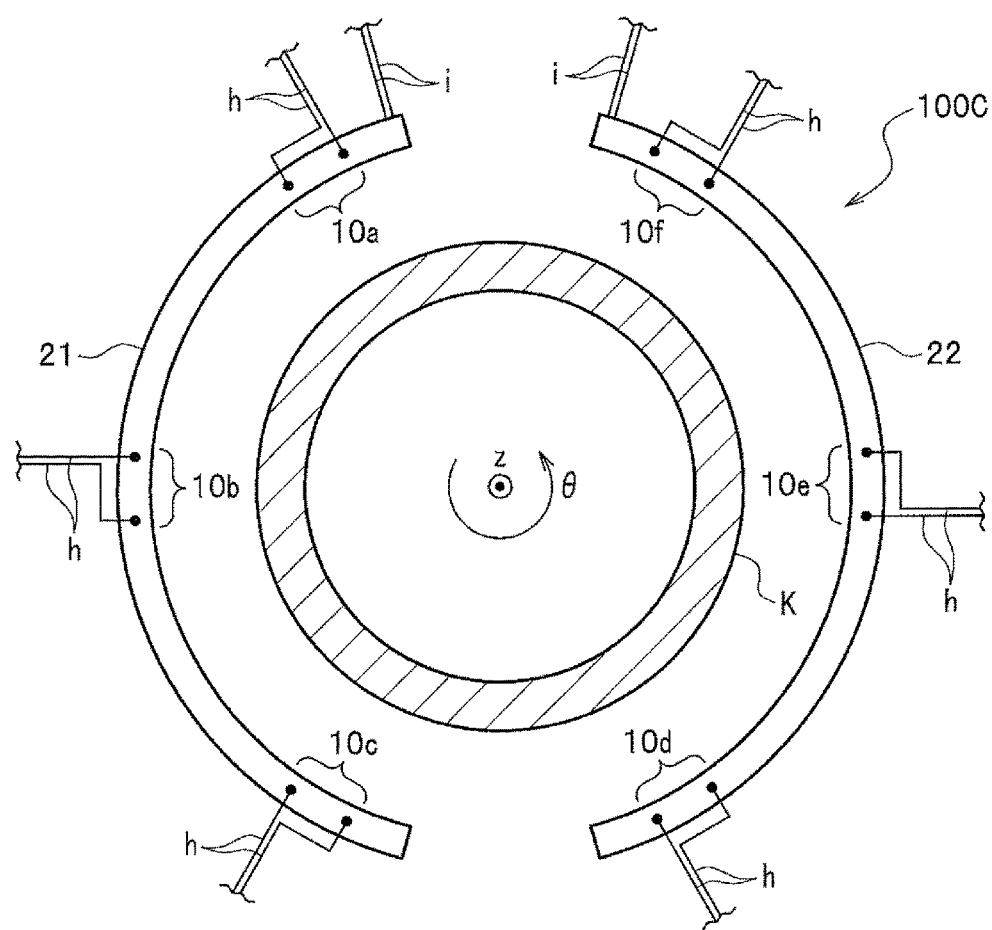
FIG. 10 is a cross-sectional view of the vicinity of a target joining position in a welding management system according to a third embodiment of the invention.

FIG. 10 is a cross-sectional view of the vicinity of the target joining position K.

As shown in FIG. 10, a welding management system 100C includes the local magnetic sensors 10a to 10f provided around the target joining position K and the correction magnetic sensors 21 and 22 curved to surround the target joining position K. Parts of the correction magnetic sensors 21 and 22 in a circumferential direction also function as the local magnetic sensors 10a to 10f.

Specifically, a part of the correction magnetic sensor 20 having a semicircular shape in a plan view is connected to the data processing unit 30 (see FIG. 1) via a pair of wires h. The "part" is provided at six positions of the correction magnetic sensor 20 in the circumferential direction corresponding to the local magnetic sensors 10a to 10f. Then, information of a joining state in the target joining position K is generated based on a difference at every time point between a detection value of each of the local magnetic sensors 10a to 10f and a detection value of the correction magnetic sensors 21 and 22.

<Effect>

According to the third embodiment, the correction magnetic sensors 21 and 22 also serve as a space used for providing the local magnetic sensors 10a to 10f. Therefore, a space for providing a "magnetic detection unit" (the local magnetic sensors 10a to 10f and the correction magnetic sensors 21 and 22) can be reduced compared to the first embodiment.

In addition, according to the third embodiment, it is not necessary to wind additional coils (the local magnetic sensors) on the correction magnetic sensors 21 and 22 at the time of providing the local magnetic sensors 10a to 10f. Therefore, labor and cost can be reduced compared to the second embodiment (see FIG. 9).

Fourth Embodiment

The fourth embodiment is different from the first embodiment in a manner of using detection values of the correction magnetic sensors 21 and 22 when the data processing unit 30D (see FIG. 11) generates information of a joining state. The others are the same as the first embodiment. Therefore, a difference from the first embodiment will be described and a description of repeated parts will be omitted.

Figure 11:
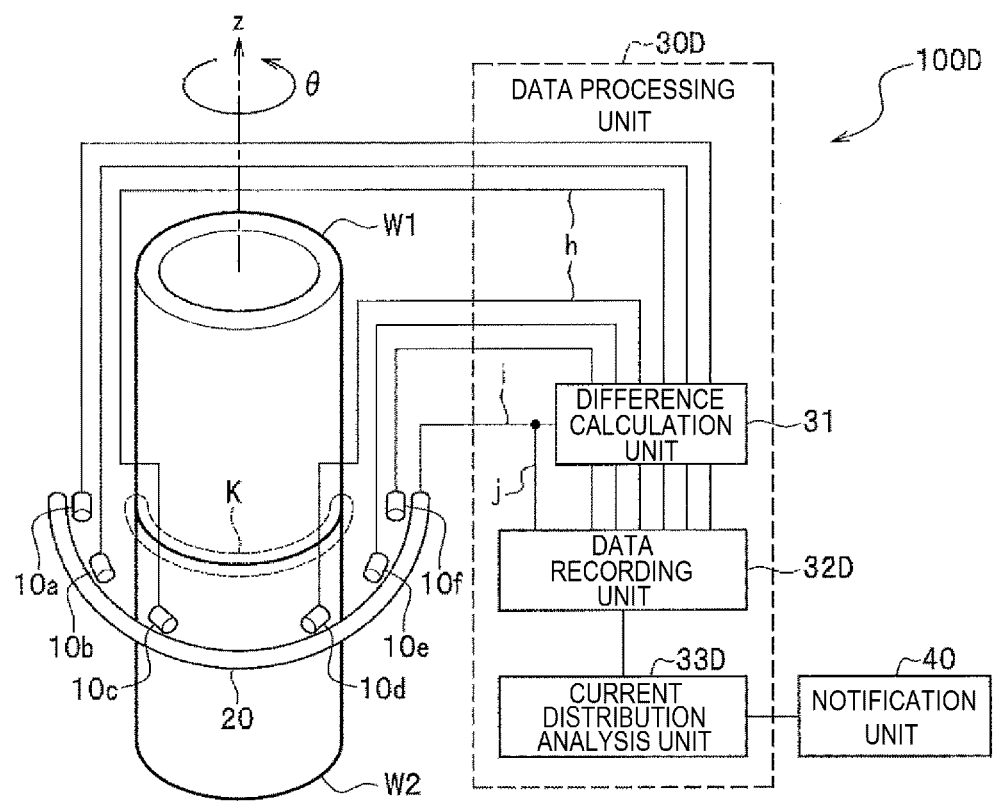
FIG. 11 is a view showing a welding management system according to a fourth embodiment of the invention.

FIG. 11 is a view showing a welding management system 100D according to the fourth embodiment.

As shown in FIG. 11, a data processing unit 30D of the welding management system 100D includes the difference calculation unit 31, a data recording unit 32D, and a current distribution analysis unit 33D.

A configuration and function of the difference calculation unit 31 are the same as those in the first embodiment.

The data recording unit 32D is connected to the difference calculation unit 31 and is also connected to the correction magnetic sensor 20 via a wire j. That is, in addition to a calculation result (a difference between each of the local magnetic sensors 10a to 10f and the correction magnetic sensor 20) of the difference calculation unit 31, a detection value of the correction magnetic sensor 20 is also input into the data recording unit 32D.

The current distribution analysis unit 33D performs predetermined processing based on data recorded (stored) in the data recording unit 32D. For example, similar to the first embodiment, the current distribution analysis unit 33D calculates time integration values (areas of the shaded portions in FIG. 4D) of absolute values of differences ΔV that are calculated by the difference calculation unit 31. When one of the time integration values is equal to or larger than a predetermined threshold, the current distribution analysis unit 33D determines that "defective welding" occurs in the target joining position K.

When a detection value of the correction magnetic sensor 20 at a peak time or the like of a welding current deviates from a predetermined range, the current distribution analysis unit 33D also determines that "defective welding" occurs in the target joining position K. For example, when abnormality occurs in the first electrode F (see FIG. 2) or the second electrodes U1 and U2 (see FIG. 2) that are used for welding, the detection value of the correction magnetic sensor 20 may become too large or too small. Defective welding can also be detected in such a case according to the present embodiment.

Alternatively, the differences ΔV (differences between detection values of the local magnetic sensors 10a to 10f and the detection value of the correction magnetic sensor 20) and the detection value of the correction magnetic sensor 20 may be analyzed as a set of data. Welding quality may be determined based on a mutual relationship between the differences ΔV and the detection value of the correction magnetic sensor 20.

For example, the larger the detection value of the correction magnetic sensor 20 when a predetermined time is elapsed (at the peak time of the welding current) after welding is started, the larger a threshold at the time of determination based on the differences ΔV may be.

Alternatively, the larger the detection value of the correction magnetic sensor 20 when a predetermined time is elapsed after welding is started, the smaller the threshold at the time of determination based on the differences ΔV may be. An administrator determines in advance whether to perform any one processing in the above-described two cases based on a predetermined welding condition.

In this manner, the data processing unit 30D generates information of a joining state of the target joining position K based on a waveform of the detection value of the correction magnetic sensor 20 and the differences ΔV.

<Effect>

According to the fourth embodiment, in addition to analyzing uniformity of current distribution, the detection value of the correction magnetic sensor 20 is also analyzed. For example, when the detection value of the correction magnetic sensor 20 is an induced voltage, the detection value is proportional to a differential value of a current flowing through the target joining position K. When the detection value of the correction magnetic sensor 20 is magnetic flux density, the detection value is proportional to a current flowing through the target joining position K.

Therefore, welding quality can be determined based on a magnitude or a waveform shape of the detection value of the correction magnetic sensor 20. That is, according to the fourth embodiment, welding quality can be determined more appropriately than the first embodiment.

Fifth Embodiment

Figure 12:
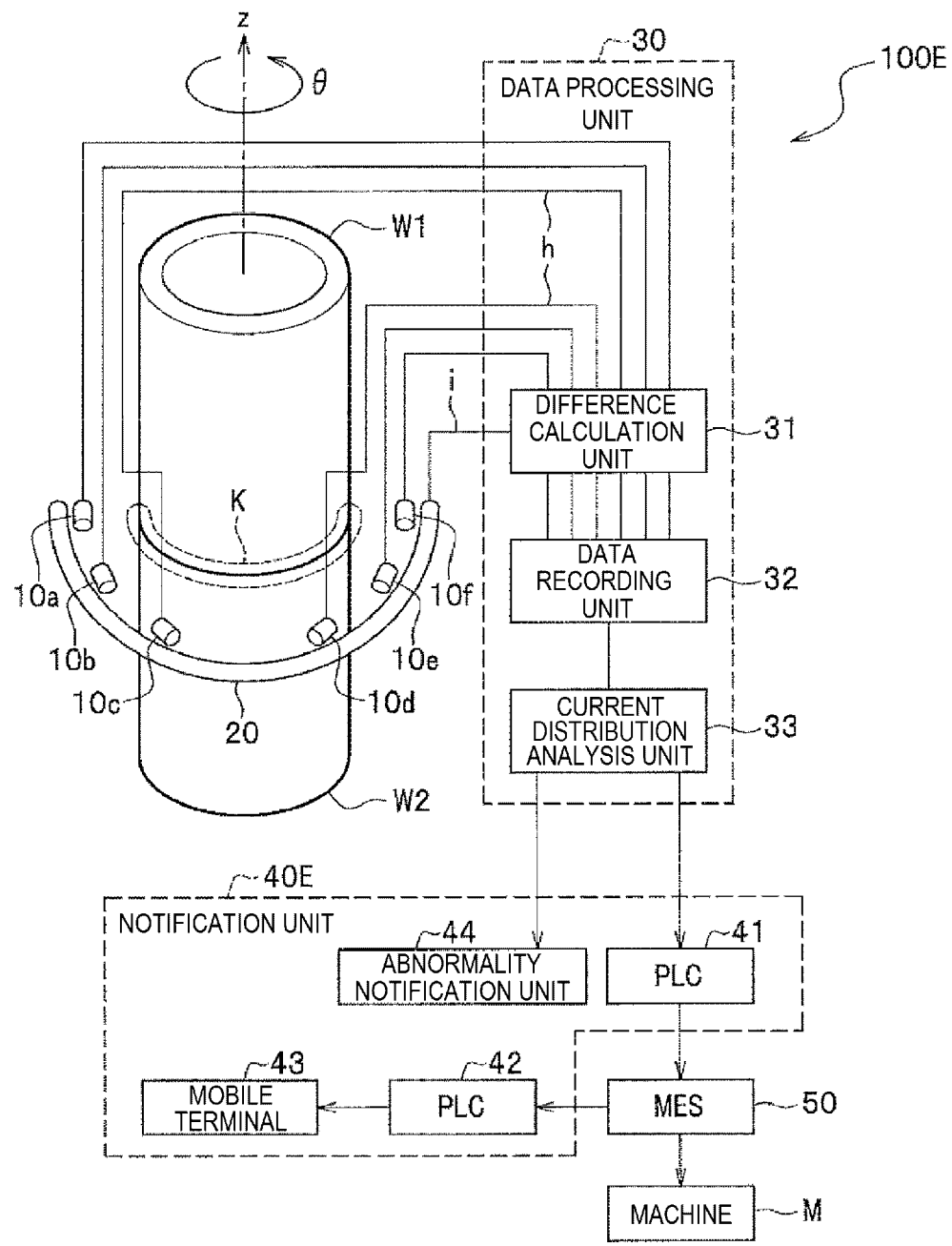
FIG. 12 is a view showing a welding management system according to a fifth embodiment of the invention.

The fifth embodiment is different from the first embodiment in a configuration of a notification unit 40E (see FIG. 12). The other configurations are the same as the configurations in the first embodiment. Therefore, a difference from the first embodiment will be described and a description of repeated parts will be omitted.

FIG. 12 is a view showing a welding management system 100E according to the fifth embodiment.

As shown in FIG. 12, the welding management system 100E includes the local magnetic sensors 10a to 10f, the correction magnetic sensor 20, the data processing unit 30, a notification unit 40E and an MEMS 50 (Manufacturing Execution System: control unit).

The notification unit 40E includes PLC 41 and 42 (Programmable Logic Controller), a mobile terminal 43, and an abnormality notification unit 44.

The PLC 41 is a programmable logic control device that outputs a predetermined signal to the MES 50 based on a processing result of the data processing unit 30.

The MES 50 is a manufacturing execution system that operates a machine such as a welding machine (not shown) based on data input into the MES 50 via the PLC 41 and manufactures a welded product. That is, the MES 50 controls a machine including the welding machine (not shown) that welds the members to be welded W1 and W2 based on information generated by the data processing unit 30.

For example, when the data processing unit 30 determines that "defective welding" occurs, the MES 50 may temporarily stop the machine such as the welding machine. Then, the MES 50 restarts the machine such as the welding machine after an administrator finds out a reason for the defective welding based on an analysis result of the data processing unit 30. In addition, the MES 50 has a function of transmitting information received from the PLC 41 to the PLC 42 via the MES 50.

The PLC 42 transmits predetermined welding information to the mobile terminal 43 based on a signal that is input into the PLC 42 from the MES 50.

The mobile terminal 43 has a function of displaying predetermined welding information or sounding predetermined voice. Accordingly, an administrator who carries the mobile terminal 43 can know the welding information.

The abnormality notification unit 44 displays the predetermined welding information or sounds a buzzer as necessary based on a processing result of the data processing unit 30. Accordingly, a site supervisor or an administrator in a central management room can know the welding information.

<Effect>

According to the fifth embodiment, a determination result of the data processing unit 30 is reflected in the control of the MES 50. Therefore, when defective welding occurs in the target joining position K, for example, the MES 50 can perform processing of temporarily stopping the machine including the welding machine (not shown). A processing result of the data processing unit 30 is displayed on the mobile terminal 43 or the abnormality notification unit 44. Accordingly, a site supervisor or an administrator can know the welding information in detail.

<<Modification>>

Although the embodiments describe the welding management system 100 and the like according to the invention, the invention is not limited to the embodiments, and various modifications can be made.

For example, although the first embodiment describes a configuration in which the local magnetic sensors 10a to 10f are provided inward of the correction magnetic sensor 20 (see FIG. 1), the invention is not limited thereto. That is, the local magnetic sensors 10a to 10f may be provided outward of the correction magnetic sensor 20. In addition, local magnetic sensors provided inward of the correction magnetic sensor 20 and local magnetic sensors provided outward of the correction magnetic sensor 20 may be mixed.

Although the embodiments describe a configuration in which the local magnetic sensors 10a to 10f are provided at equal intervals in the circumferential direction, the invention is not limited thereto. That is, intervals between adjacent local magnetic sensors in the circumferential direction may be different.

Although the embodiments describe a case in which distances between the target joining position K and the local magnetic sensors 10a to 10f are equal for each of the local magnetic sensors 10a to 10f, the invention is not limited thereto. That is, local magnetic sensors with different distances between the target joining position K and the local magnetic sensors may be mixed. It is not necessary to bring the local magnetic sensors 10a to 10f close to the correction magnetic sensor 20.

Although the embodiments describe a case in which the local magnetic sensors 10a to 10f have coils or the correction magnetic sensor 20 has a coil, the invention is not limited thereto. For example, a Hall sensor or a magneto-resistance sensor may be used as the local magnetic sensors 10a to 10f and the correction magnetic sensor 20.

Although the embodiments describe a case in which the detection value of the local magnetic sensors 10a to 10f or the correction magnetic sensor 20 is an induced voltage, the invention is not limited thereto. For example, the detection value of the local magnetic sensors 10a to 10f or the correction magnetic sensor 20 may be magnetic flux density. In such a case, processing of the data processing unit 30 is the same as in the first embodiment.

The embodiments may be combined as appropriate. For example, the second embodiment and the fourth embodiment may be combined. That is, in a configuration in which the local magnetic sensors 10a to 10f are wound on the correction magnetic sensor 20 (the second embodiment), the data processing unit 30 may generate information of a joining state based on a waveform of the detection value of the correction magnetic sensor 20 and the differences ΔV.

Although the embodiments describe a case in which an external shape of the members to be welded W1 and W2 is columnar (for example, the external shape is cylindrical in FIG. 1 and quadrangular columnar in FIG. 8), the invention is not limited thereto. For example, the members to be welded may have a flat plate shape.

Although the embodiments describe a case in which resistance welding is performed, the invention is not limited thereto. For example, the embodiments may also be applied to arc welding, laser welding, and friction stir welding.

The embodiments are described in detail for easy understanding of the invention, and the invention is not necessarily limited to those including all the configurations described above. Apart of a configuration of each embodiment can be added, deleted, or replaced with another configuration. The mechanisms and configurations described above are ones considered to be necessary for description, and not all of the mechanisms and configurations required in a product are necessarily shown.

REFERENCE SIGN LIST

100: welding management system
100A, 100B, 100C, 100D, 100E: welding management system
10a, 10b, 10c, 10d, 10e, 10f: local magnetic sensor (magnetic detection unit, first magnetic detection unit)
20, 21, 22: correction magnetic sensor (magnetic detection unit, second magnetic detection unit)
30, 30D: data processing unit
31: difference calculation unit
32, 32D: data recording unit
33, 33D: current distribution analysis unit
40, 40E: notification unit
50: MEMS (control unit)
h: wire (pair of wires)
K: target joining position
La, Lb, Lc, Ld, Le, Lf: light source (notification unit)
W1, W2: member to be welded

The invention claimed is:

1. A welding management system comprising:
a magnetic detection unit that detects magnetism generated around a target joining position accompanying with energization to a member to be welded when the member to be welded is welded by heat generated accompanying with the energization;
a data processing unit that processes a detection value of the magnetic detection unit,
wherein the magnetic detection unit includes:
a plurality of first magnetic detection units provided around the target joining position; and
a second magnetic detection unit curved to surround the target joining position, and
wherein the data processing unit generates information of a joining state of the target joining position based on a difference between each of detection values of the plurality of the first magnetic detection units and a detection value of the second magnetic detection unit; and
a notification unit that notifies of the information generated by the data processing unit,
wherein, when defective welding occurs in the target joining position, the notification unit displays one of the first magnetic detection units that corresponds to a position where the defective welding occurs and an other one of the first magnetic detection units in a differentiated manner.

2. The welding management system according to claim 1, wherein a range in a circumferential direction of the second magnetic detection unit that is curved to surround the target joining position covers a position in the circumferential direction of each of the plurality of the first magnetic detection units.

3. A welding management system comprising:
a magnetic detection unit that detects magnetism generated around a target joining position accompanying with energization to a member to be welded when the member to be welded is welded by heat generated accompanying with the energization;
a data processing unit that processes a detection value of the magnetic detection unit, wherein the magnetic detection unit includes:
   a plurality of first magnetic detection units provided around the target joining position; and
   a second magnetic detection unit curved to surround the target joining position, and
wherein the data processing unit generates information of a joining state of the target joining position based on a difference between each of detection values of the plurality of the first magnetic detection units and a detection value of the second magnetic detection unit; and
a notification unit that notifies of the information generated by the data processing unit,
wherein the notification unit displays the detection values of the plurality of first magnetic detection units as a radar chart with the detection value of the second magnetic detection unit as a reference.

4. The welding management system according to claim 1, wherein
   each of the plurality of the first magnetic detection units and the second magnetic detection unit have a coil for magnetic detection.

5. The welding management system according to claim 4, wherein
   the plurality of the first magnetic detection units are separately wound on the second magnetic detection unit that is curved to surround the target joining position.

6. The welding management system according to claim 4, wherein a part in a circumferential direction of the second magnetic detection unit that is curved to surround the target joining position also functions as the first magnetic detection units, and
wherein the part of the second magnetic detection unit is connected to the data processing unit via a pair of wires and the part is provided at a plurality of positions on the second magnetic detection unit in the circumferential direction.

7. The welding management system according to claim 1, wherein the data processing unit generates the information of a joining state of the target joining position based on a waveform of the detection value of the second magnetic detection unit and the difference.

8. A welding management system comprising:
   a magnetic detection unit that detects magnetism generated around a target joining position accompanying with energization to a member to be welded when the member to be welded is welded by heat generated accompanying with the energization;
   a data processing unit that processes a detection value of the magnetic detection unit,
      wherein the magnetic detection unit includes:
         a plurality of first magnetic detection units provided around the target joining position; and
         a second magnetic detection unit curved to surround the target joining position, and
      wherein the data processing unit generates information of a joining state of the target joining position based on a difference between each of detection values of the plurality of the first magnetic detection units and a detection value of the second magnetic detection unit; and
   a control unit that controls a machine including a welding machine that welds the member to be welded based on the information generated by the data processing unit.

* * * * *